United States Patent
Hultgren et al.

(10) Patent No.: US 8,725,465 B2
(45) Date of Patent: May 13, 2014

(54) DENTAL MODELING SYSTEM AND METHOD

(76) Inventors: Bruce Willard Hultgren, Victoria, MN (US); Michael Craig Marshall, Prior Lake, MN (US)

( * ) Notice: Subject to any disclaimer, the term of this patent is extended or adjusted under 35 U.S.C. 154(b) by 0 days.

(21) Appl. No.: 12/540,233

(22) Filed: Aug. 12, 2009

(65) Prior Publication Data

US 2010/0145664 A1    Jun. 10, 2010

Related U.S. Application Data

(63) Continuation of application No. 12/359,993, filed on Jan. 26, 2009, now abandoned, which is a continuation of application No. 12/169,567, filed on Jul. 8, 2008, now abandoned, which is a continuation of application No. 11/999,891, filed on Dec. 7, 2007, now abandoned, which is a continuation of application No. 11/800,430, filed on May 4, 2007, now abandoned.

(60) Provisional application No. 60/797,911, filed on May 4, 2006.

(51) Int. Cl.
*G06F 17/50* (2006.01)

(52) U.S. Cl.
USPC .................................................. 703/1; 433/24

(58) Field of Classification Search
USPC .................................................. 703/1; 433/24
See application file for complete search history.

(56) References Cited

U.S. PATENT DOCUMENTS

| | | | |
|---|---|---|---|
| 5,882,192 A | 3/1999 | Bergersen | |
| 6,217,334 B1 | 4/2001 | Hultgren | |
| 6,250,918 B1 * | 6/2001 | Sachdeva et al. | 433/24 |
| 6,413,083 B1 | 7/2002 | Hamilton | |
| 6,579,059 B2 | 6/2003 | Chen | |
| 6,602,070 B2 | 8/2003 | Miller et al. | |
| 6,632,089 B2 | 10/2003 | Rubbert et al. | |
| 7,029,275 B2 | 4/2006 | Rubbert et al. | |
| 7,080,979 B2 | 7/2006 | Rubbert et al. | |
| 7,210,929 B2 * | 5/2007 | Raby et al | 433/24 |
| 7,744,369 B2 | 6/2010 | Imgrund et al. | |
| 8,108,189 B2 | 1/2012 | Chelnokov et al. | |
| 8,401,826 B2 * | 3/2013 | Cheng et al. | 703/1 |
| 2002/0025503 A1 | 2/2002 | Chapoulaud et al. | |

(Continued)

FOREIGN PATENT DOCUMENTS

| | | |
|---|---|---|
| EP | 0020951 AO | 2/2009 |
| WO | WO 94/10935 | 5/1994 |

(Continued)

OTHER PUBLICATIONS

Kazuo Hayashi, Meiri Hamaya, Itaru Mizoguchi, "Simulation Study for a Finite Helical Axis Analysis of Tooth Movement" Angle Orthodontist, vol. 75, No. 3, 2005, pp. 350-355.*

(Continued)

*Primary Examiner* — Dwin M Craig (74) *Attorney, Agent, or Firm* — Merchant & Gould PC (57) ABSTRACT

A method for simulating tooth movement utilizes electronic modeling to represent the teeth. Instant centers of rotation are determined and projected paths of movement are plotted. The electronic model provides improved precision and provides a method for simulating movement in three dimensions. The movement from growth and/or correction is shown with the electronic model. The simulation provides for improved correction.

17 Claims, 10 Drawing Sheets

(56) References Cited

U.S. PATENT DOCUMENTS

| | | | |
|---|---|---|---|
| 2002/0031742 A1 | 3/2002 | Hamilton | |
| 2004/0029068 A1 | 2/2004 | Sachdeva et al. | |
| 2004/0038168 A1 | 2/2004 | Choi et al. | |
| 2004/0259049 A1 | 12/2004 | Kopelman et al. | |
| 2006/0263739 A1* | 11/2006 | Sporbert et al. | 433/24 |
| 2006/0263741 A1* | 11/2006 | Imgrund et al. | 433/24 |
| 2008/0057462 A1 | 3/2008 | Kitching et al. | |
| 2008/0286712 A1 | 11/2008 | Imgrund et al. | |
| 2009/0061382 A1 | 3/2009 | Wen | |
| 2009/0098502 A1 | 4/2009 | Andreiko | |
| 2010/0145664 A1* | 6/2010 | Hultgren et al. | 703/1 |
| 2010/0169057 A1 | 7/2010 | Hultgren et al. | |
| 2011/0189625 A1 | 8/2011 | Hultgren et al. | |
| 2011/0191075 A1 | 8/2011 | Hultgren et al. | |
| 2011/0244415 A1 | 10/2011 | Batesole | |

FOREIGN PATENT DOCUMENTS

| | | | |
|---|---|---|---|
| WO | WO 03/094102 A1 | 11/2003 | |
| WO | 2007130573 A2 | 11/2007 | |
| WO | 2007130574 A1 | 11/2007 | |

OTHER PUBLICATIONS

Vardimon, A. et al., "Cortical bone remodeling/tooth movement ratio during maxillary incisor retraction with tip versus torque movements," *Am. J. Orthod. Dentofacial Orthop.*, vol. 114, No. 5, pp. 520-529 (Nov. 1998).

George Papaioannou, NPL Publication, "Joints, Biomechanis of", 63 pages, (Feb. 2006).

Jan Edwards, "Rotation and Translation of the Jaw During Speech", 16 pages, (1990).

Kazuo Hayashi, "Simulation Study for a Finite Helical Axis Analysis of Tooth Movement" 6 pages, (2005).

International Search Report in PCT/US2007/010839 mailed Oct. 17, 2007.

International Search Report in PCT/US2007/010838 mailed Jul. 11, 2007.

Hultgren et al., U.S. Appl. No. 11/800,430, "Dental Modeling System and Method." May 4, 2007.

Isaacson, Robert J. et al., U.S. Appl. No. 11/999,891, "Dental Modeling System and Method." Dec. 7, 2007.

Isaacson, Robert J. et al., U.S. Appl. No. 12/169,567, "Dental Modeling System and Method." Jul. 8, 2008.

Isaacson, Robert J. et al., U.S. Appl. No. 12/359,993 "Dental Modeling System and Method." Jan. 26, 2009.

Hultgren, Bruce Willard, U.S. Appl. No. 12/299,581, "Dental Modeling System and Method." Nov. 4, 2008.

Isaacson, Robert J. et al., U.S. Appl. No. 11/999,892, "System and Method for Evaluating Orthodontic Treatment." Dec. 7, 2007.

Isaacson, Robert J. et al., U.S. Appl. No. 11/800,449, "System and Method for Evaluating Orthodontic Treatment." May 4, 2007.

Isaacson, Robert J. et al., U.S. Appl. No. 13/383,408, "System and Method for Evaluating Orthodontic Treatment." Jan. 10, 2012.

Isaacson, Robert J. et al., U.S. Appl. No. 13/623,754, "System and Method for Evaluating Orthodontic Treatment." Sep. 20, 2012.

* cited by examiner

DENTAL MODELING SYSTEM AND METHOD

BACKGROUND OF THE INVENTION

1. Field of the Invention

The present invention relates to a method and system for simulating movement of a patient's jaw and teeth.

2. Description of the Prior Art

In the field of orthodontics, simulation is important for treatment and correction. If the manner in which the teeth and jaw may form and grow is known, the dental practitioner is better able to diagnose problems and identify potential problems. In addition, the limits of moving teeth through braces and other correction techniques become more apparent and treatment may be carried out with more precision and greater chance of success.

Prior simulation techniques consisted of the dental practitioner observing the patient's teeth and utilizing the practitioner's knowledge and judgment to predict how the teeth would move by estimating the effects of braces and other corrective techniques. Although usually successful in correcting at least some of the structural problems, greater success rates are possible with additional information and knowledge about the patient's likely tooth movement both with and without correction.

Efforts to model tooth movement have been developed that proved to be a great aid for practitioners. Some models involve linear tooth growth, especially for those in the lower jaw. However, studies and modeling reveal that tooth movement and growth is not usually truly linearly translational. Although such modeling is helpful, with greater precision, more accurate simulations could be achieved.

Other theories that have been developed involve identifying an imaginary center of rotation for a particular tooth. Such theories as stated in papers by Pilgrim, Moses, Erdman and Hultgren, utilized instant centers of rotation to predict tooth movement along an arc centered on the instant center of rotation. It is believed that such a model is typically a better predictor of actual tooth movement than a model using straight line movement.

A further model simulates tooth movement as being governed by a linkage. The model predicts growth that is not straight line, but the arc along which the tooth moves is not centered on a single center of rotation and therefore the tooth behaves as if it was a segment of a linkage, for example, following a path as if it were mounted on one link of a four bar linkage.

Although such models have proven to be successful in providing guidance for predicting tooth growth and movement, implementation in a practical manner has proven difficult. Current techniques do not provide for accurately tracking tooth movement with sufficient precision and their relationship to the tooth's reference points. Markers and/or landmarks are necessary to ensure that the movement of the tooth or of a specific portion of the tooth are tracked. While such markers provide for improved modeling and tracking, the insertion and placement of such markers and tracking of the markers relative to one another is intrusive and only allows tracking of the marker rather than the entire tooth. A portion of the tooth moves with the marker, but it is possible that the orientation in one or more planes may have changed or other portions of the tooth may have moved in a different manner.

A further problem with such markers and/or landmarks is the precision possible in tracking the changes in position. Heretofore, tracking of markers in teeth has generally been accomplished by taking x-rays of the markers and teeth and outlining the teeth and/or markers to establish a current position. The insertion and removal of markers is intrusive and inconvenient for the patient, requiring an additional procedure. While such methods do provide for tracking of position and changes, the accuracy of such methods is decreased due to quality and resolution available for the images and the inaccuracy from manually outlining and precisely locating the markers and/or structural landmarks. As the accuracy and precision are critical for predicting small movements and in locating instant centers of rotation, such tools may not be an acceptable simulator of the teeth and their movement. Due to the precise measurements and the small distances involved, even minor errors can have a drastic adverse affect on the position of an instant center of rotation and therefore, the entire model and movement simulation, increasing the possibility for improper diagnosis and treatment.

Techniques have also been developed in orthodontics modeling to create a digital three dimensional model by scanning a casting of a patient's teeth and gums. The digital EMODEL™ digital model system provides a precise high resolution digital map of the teeth and gums, but its use has been limited in creating prostheses. Such three dimensional digital images have been used as a starting point in treatment, but have not been used to project and simulate growth and movement.

It can be seen then that a new and improved system is needed that overcomes the problems and deficiencies associated with the prior art modeling systems and methods. A system and method is needed that precisely models position and accurately simulates movement of the patient's jaw and teeth. In addition, such a system and method should provide minimal intrusion for the patient. Such a system and method should also be practical to utilize and should achieve sufficient precision and reliability for accurate simulation by the dental practitioner to diagnose problems and prescribe proper treatment. The present invention addresses these as well as other problems associated with simulating tooth growth and movement.

SUMMARY OF THE INVENTION

The present invention is directed to a system and method for modeling tooth movement. Electronic modeling is used to create a precise and accurate three dimensional virtual model of the teeth.

In creating an electronic virtual model, a casting of the patient's teeth is taken and a plaster model created. A scanner is used to digitize a three dimensional image of the patient's mouth for modeling. Alternatively, three dimensional high resolution digital scanners, such as CT scanners, intra-oral scanners, cone beam scanners or other digital capture devices may scan the patient's facial structure to create a three dimensional virtual model. A computer database stores the digital image and the image may be viewed as a three dimensional virtual model that may be manipulated on the computer screen. Moreover, the system provides for separating the teeth into discrete elements for modeling movement of an individual tooth and for modeling movement of all teeth to help in providing proper diagnosis for treatment and correction. The images may be manipulated to model projected growth or movement over time.

According to the present invention, modeling of tooth movement is accomplished by identifying an instant center of rotation for a particular tooth or other structure of the patient's jaw. The movement that the tooth would follow at that point in time is an arc centered about the instant center of rotation. The instant center of rotation can be plotted in three dimensions so that the model tooth movement follows the surface of an imaginary sphere centered about the instant center of rotation. As the image is digitized, the teeth or other structures and their respective instant centers of rotation can be mathematically represented with a set of coordinates so that the plotting of movement is accomplished with great precision. Locating the instant center of rotation is accomplished utilizing a number of factors based on the patient's tooth and jaw physiology and the knowledge and experience of the dental practitioner. It can be appreciated that the instant center of rotation varies from patient to patient and an instant center may be above or below the position of the tooth as well as to one side or the other, or forward or behind a tooth. The position may be quite close to the tooth or may approach infinity so that the virtual tooth substantially models straight line movement.

The position of the instant center of rotation may be moved to reflect different types and sets forces applied to the tooth, such as movement to changing position of surrounding teeth or the application of braces to the tooth. Instant centers may also be determined for larger structures in the mouth or jaw whose movement may be simulated. Moreover, the forces of growth and passage of time are typically different than the forces acting on the tooth or structure due to correction. Therefore, depending on the evaluation and analysis required, different instant centers of rotation may be determined for analyzing different sets of kinematic and dynamic factors. As an instant center of rotation shifts, the projected path also shifts and the radius from the instant center to the projected arc may lengthen or shorten. With the digital image stored, the treatment and the modeling provides for application of varied forces and in various directions with different projected paths of movement so that the diagnosis and treatment may be optimized.

The present invention also contemplates modeling for movement of some teeth wherein a tooth substantially pivots about two axes of rotation and models the movement of a virtual four bar linkage. The modeling is similar to the modeling for rotation about a single axis, but two points on the tooth or other structure are plotted. Using the same techniques discussed above, the instant centers of rotation are located for both points on the tooth. The entire tooth is then moved with each plotted point on the tooth following a path of movement along an arc centered on the associated instant center of rotation, so that the tooth substantially follows the movement of a four bar linkage type model.

These features of novelty and various other advantages that characterize the invention are pointed out with particularity in the claims annexed hereto and forming a part hereof. However, for a better understanding of the invention, its advantages, and the objects obtained by its use, reference should be made to the drawings that form a further part hereof, and to the accompanying descriptive matter, in which there is illustrated and described a preferred embodiment of the invention.

BRIEF DESCRIPTION OF THE DRAWINGS

Referring now to the drawings, wherein like reference numerals and letters indicate corresponding structure throughout the several views.

DETAILED DESCRIPTION OF THE PREFERRED EMBODIMENT

Figure 1:
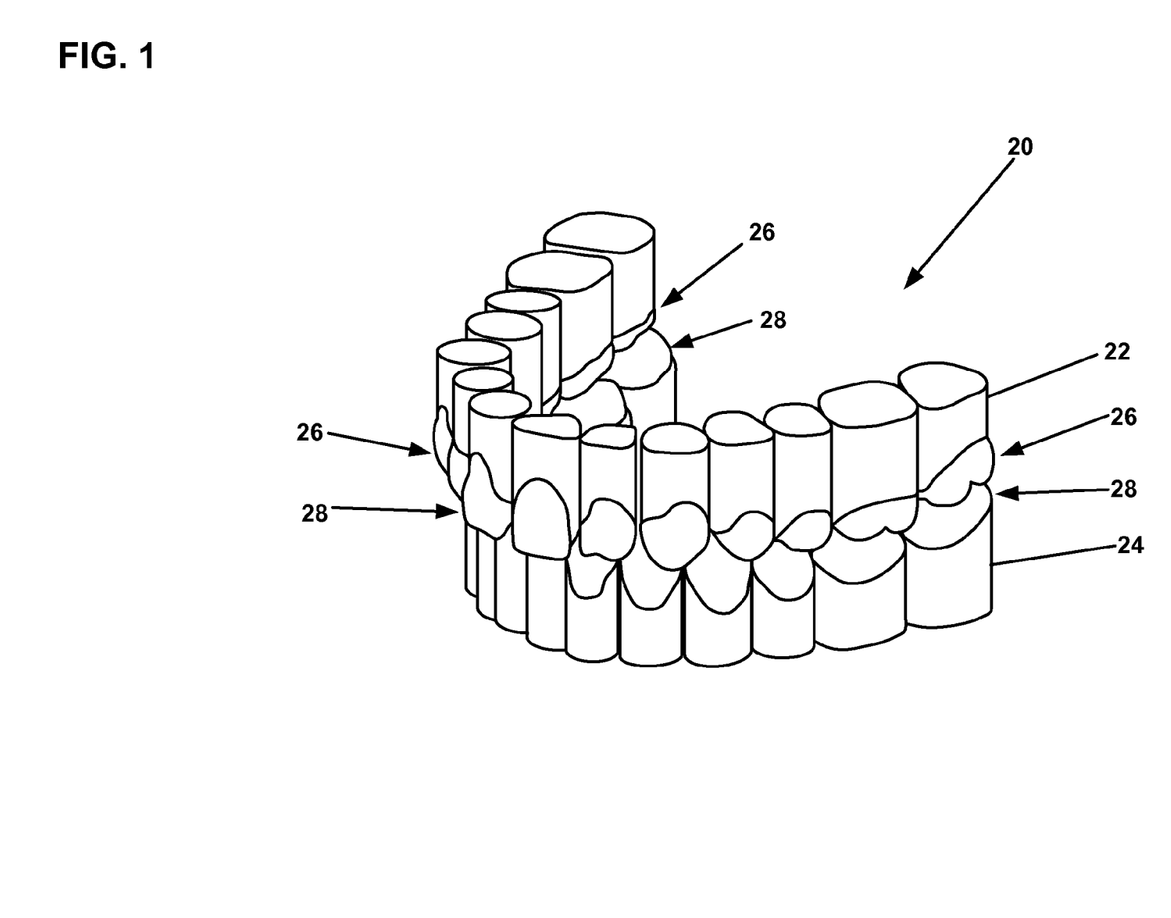
FIG. 1 is a perspective view of a three-dimensional digital model of a patient's dentition.
Figure 2:
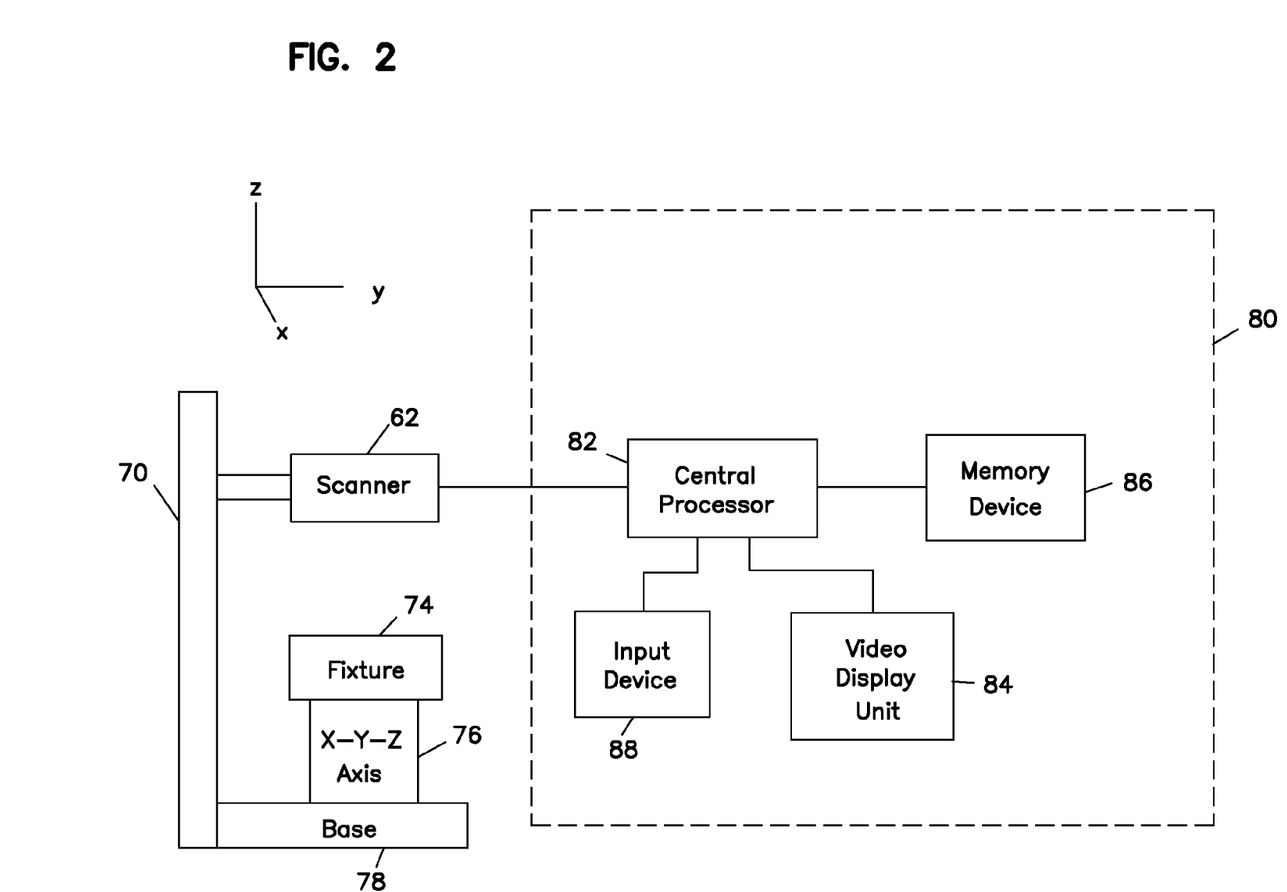
FIG. 2 is a diagrammatic view of a system for modeling tooth movement according to the principles of the present invention.

Referring now to the drawings, and in particular to FIG. 1, there is shown a digital image of a patient's dentition 20 including an upper arch having a portion of the upper gums 22, and the exposed surfaces of the upper teeth 26. In a similar manner, a lower arch including a portion of the teeth and lower gums 24 is also created in a digitized model along with the exposed upper surfaces of the lower teeth 28. Such an image of the dentition 20 is digitized and provides a virtual three dimensional image of the patient's teeth for diagnosis, treatment and correction. Such a method and system for creating such a virtual image of the patient's mouth is shown and described in U.S. Pat. No. 6,579,059, incorporated herein by reference. One method of creating digital images is taking a casting of the patient's teeth and creating a plaster model and scanning the plaster cast. The digitizing system 70 is shown in FIG. 2 and includes a scanner 72 that passes a laser over the plaster model held by fixture 74. A rotatable support 76 mounts on a base 78 and provides for moving the plaster model relative to the scanner so that the outer contour of the patient's teeth and gums can be stored in a digital format of a memory device 86. A central processor 82 provides for converting the data from the scanner to a digital image of the exterior of the patient's teeth and gums. An input device 80 provides for manipulating images 88 and a display 84 provides a screen for viewing the virtual image of the teeth and gums. It can be appreciated that the digital image provides for modeling with each tooth represented by sets of coordinates in three dimensions so that the tooth may be manipulated independently such as to model tooth movement. Moreover, when a digitized virtual model is created in three dimensions, mathematical calculations may be performed and then displayed to provide the dentist or orthodontist with sufficient precision for meaningful diagnosis and treatment. Mapping in three dimensions and greater precision provide for meaningful treatment that is not possible with prior methods based on markers and/or x-rays.

More recently, high resolution three dimensional scanners have been developed that provide direct three dimensional craniofacial imaging that may be used to create a digital representation of a patient's teeth with a high degree of precision without plaster casts and without using landmarks or markers. Such scanners include cone beam tomography scanners, intra-oral scanners, CT scanners and other technologies that provide high resolution precision three dimensional digital models. Examples of commercial available scanners include cone beam scanners sold under the trade names ILUMA™ from Kodak and i-CAT from Imaging Sciences International. Cone beam tomography scanners are well suited for such applications as they emit lower radiation than traditional dental x-rays and may eliminate the need for creating plaster casts.

Figure 3:
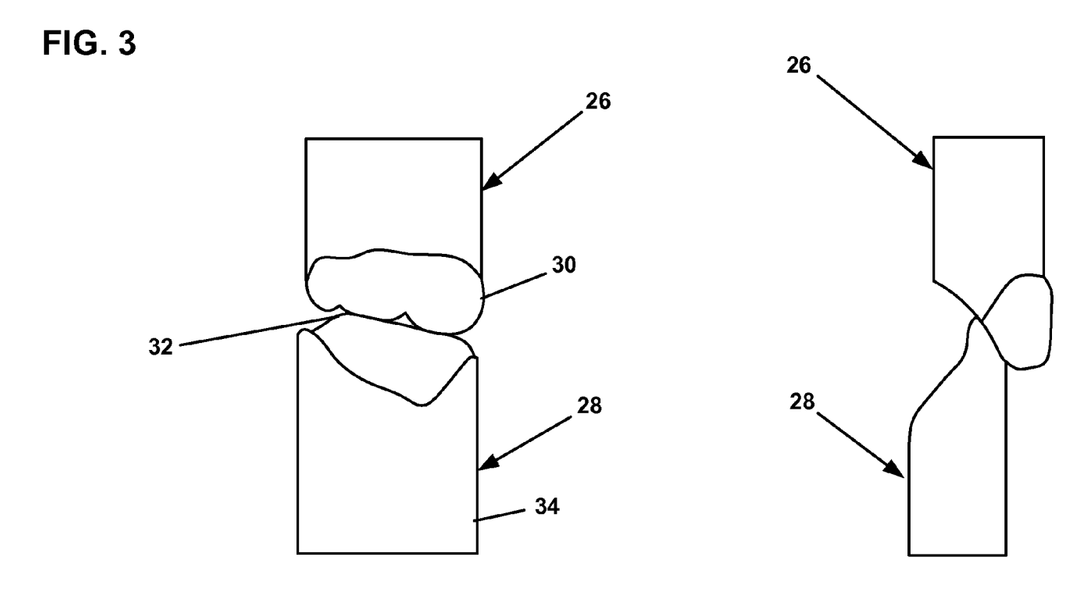
FIG. 3 is a diagrammatic view of a portion of the virtual model shown in FIG. 1 with an instant center of rotation shown for a selected tooth.
Figure 4:
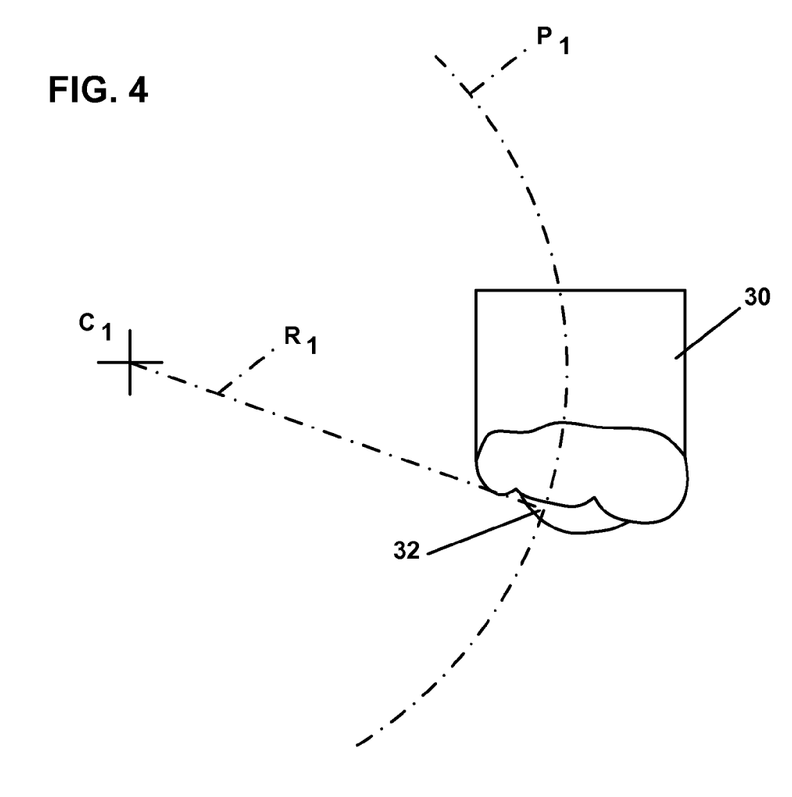
FIG. 4 is a diagrammatic view of a projected path of movement for a selected portion of the selected tooth shown in FIG. 3.

Referring now to FIG. 3, there is shown a portion of the patient's dentition including representative upper incisors and molars 26 and lower incisors and molars 28. A selected tooth 30 having a complementary lower tooth 34 shown as an upper molar in FIG. 3 is modeled and movement of the tooth may be determined. It has been found that the path of movement of a tooth may be more accurately modeled as rotating about an imaginary point, forming an axis of rotation, represented as center point C1 in FIG. 4. Each tooth has various forces acting on the tooth and other structure in the jaw that affect movement. A kinematic and dynamic analysis and synthesis is performed based on the patient's facial structures to determine the imaginary instant center. An imaginary instant center of rotation may be calculated for each tooth. In addition to an individual tooth, the jaw, groups of teeth and other structures in the jaw and mouth may also have an imaginary instant center point about which such structures move. Moreover, the forces due to growth may act differently on the tooth or structure so that a tooth or structure in a patient that is growing may have an instant center for corrective or restorative procedures and a different instant center to simulate movement for passage of time and growth. The center point C1 may be represented as a set of X, Y and Z coordinates in the digital model. The movement of the tooth 30 is limited by the gums, jaw, surrounding teeth and other structures and forces acting on it. Therefore, the movement of point 32 will occur along an arcing path P1 centered on the instant center of rotation C1. The tooth will move along this path and correction, growth or other forces acting on the tooth may direct it a distance along this path. The path may be charted along a set of coordinates in the digital model with great precision. Such a virtual model may be utilized to predict repositioning of the tooth or structure from the passage of time and growth. In addition, a virtual model that may have a different instant center of rotation may be utilized to predict repositioning of the tooth or structure due to forces applied by the other teeth and structures in the mouth or the addition of orthodontic structures. Predicting the distance along the projected path P1 that a tooth will move, a new position of the tooth 30 may be projected and also represented mathematically as a new set of coordinates stored in the memory device 86. Such a three dimensional representation may be shown and manipulated by the dental practitioner in selecting and optimizing treatment.

To determine a path of rotation for modeling the tooth and tooth movement, a point 32 on or in the tooth is selected as the tracing point for projecting a path of movement. An instant center of rotation is established with published methods and using the expertise and estimation from the dental practitioner based on features of the virtual image of the dentition 20 as well as the type and overall structure of the patient's skull and jaw. The instant center is established by analyzing the various static and dynamic forces acting on the tooth. In one embodiment, the center point C1 is selected based on the occlusal plane of the teeth 30 and 32, the structure of the patient's jaw, and patterns of movement generally associated with similar physiology. Centers of rotation have been previously charted from studies conducted using prior art markers that provide guidance for the dental practitioner locating the instant center. Similar jaw structures for comparison provide guidance to locate centers of rotation, so that the axis may be accurately approximated with the available information and an accurate virtual model of the patient's dentition 20.

Figure 7:
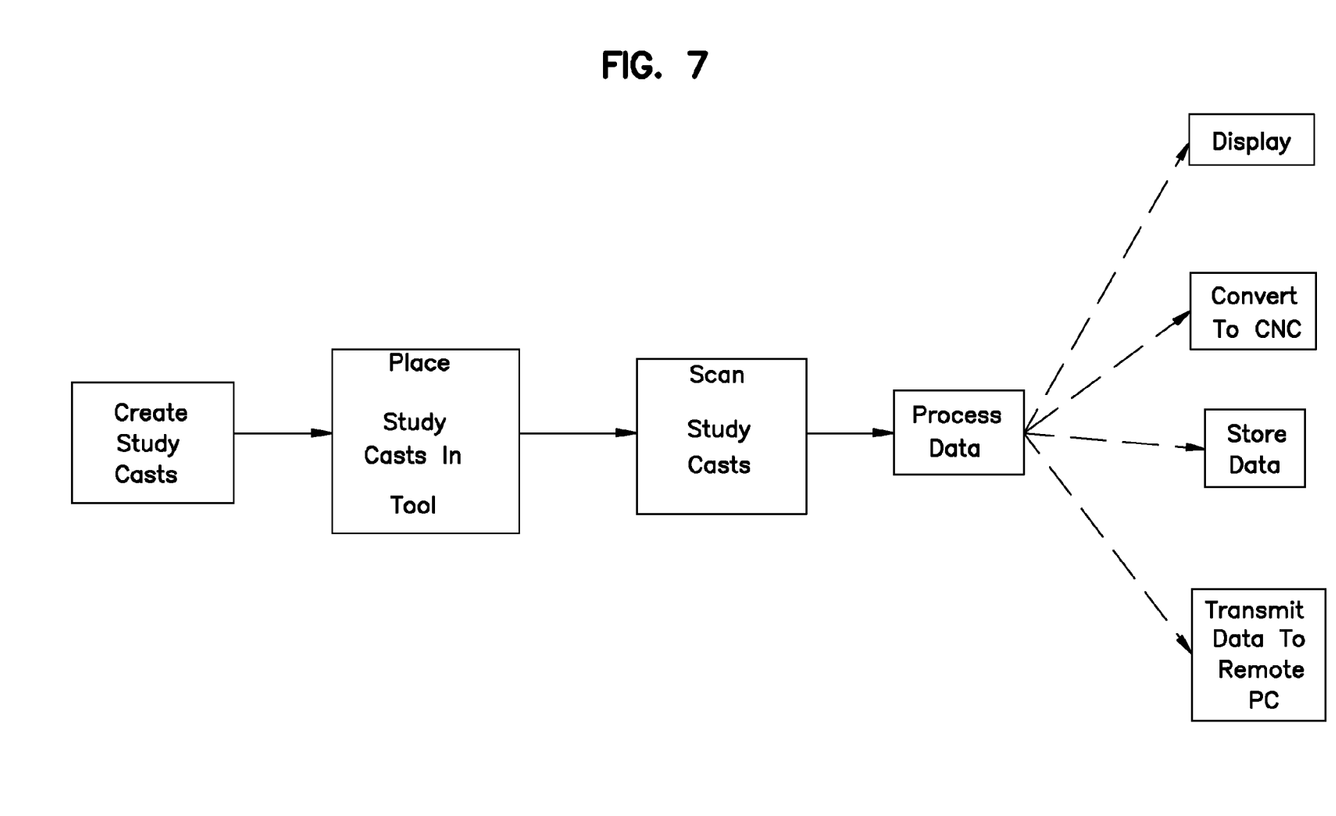
FIG. 7 shows a flow chart of the steps to create a digital model.

As shown in FIG. 7, the point of projection 32 is entered and stored as a set of coordinates in the memory device 86, shown in FIG. 2. In addition, the orientation of the remainder of the exposed portion of the tooth 30 is also entered and stored as a set of coordinates in three dimensions. This orientation is in relation to a radius R1 extending from the point of projection 32 to the center C1. As the tooth moves along the projected path of movement P1, the radius distance remains constant and the position and orientation of the tooth structure 30 translates with respect to the radius R1. A direction of movement is also determined by the dental practitioner using knowledge of the patient's physiology and the forces applied by the selected treatment.

Based on the repositioning of the tooth 30 as it rotates about the center point C1, various treatments and/or decisions may be made regarding alignment and positioning of the tooth. Moreover, by performing the same analysis on other teeth, an overall treatment plan may be devised in a coordinated manner so that treatment is more effective.

Figure 5:
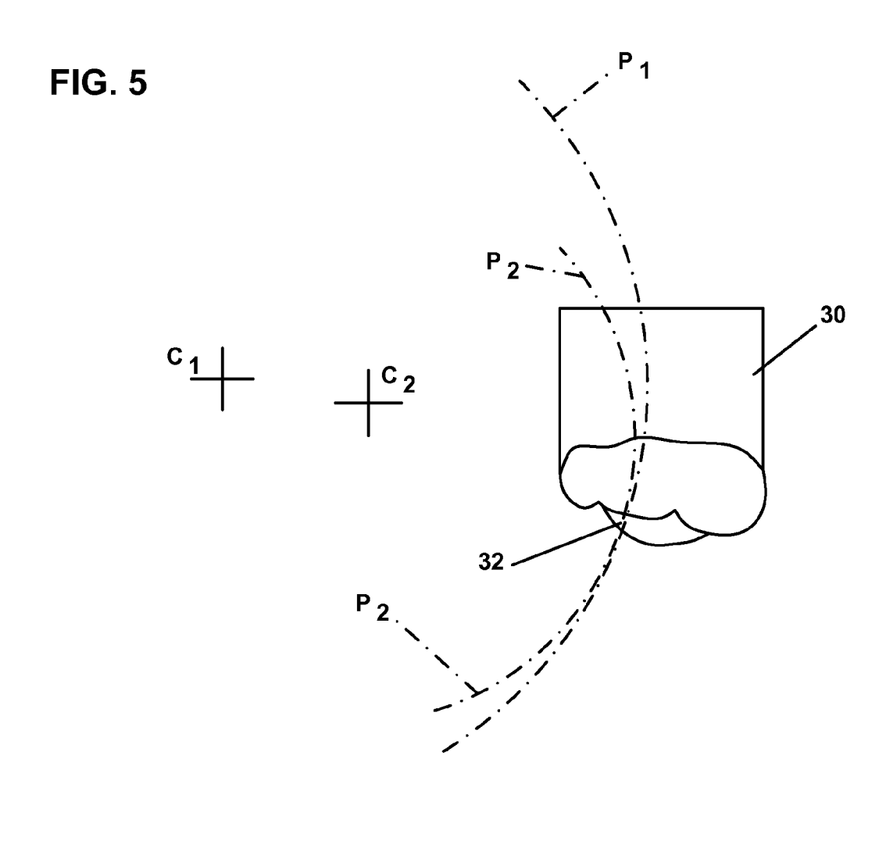
FIG. 5 is a diagrammatic view of a projected path of movement for growth.

Referring now to FIG. 5, in some instances, the rotational center of the plotted point 32 may move closer to the tooth due to changes in forces applied, such as for example, braces. For example, C1 may shift from position C1 to position C2. Therefore, the path of rotation moves from the projected path P1 to the projected path P2. The movement of the projected path allows for recalculating movement and more precise diagnosis and treatment for more properly positioning the teeth. Although the center is shown to be moved closer to the tooth 30 in FIG. 5, it can be appreciated that the center of rotation may shift in any direction. Moreover, the instance center may be above, below, behind or in front of the tooth and that the illustrated center C1 and C2 and the corresponding paths P1 and P2 and radial cords R1 and R2 are shown as examples only. Positioning will depend upon the particular physiology of the patient's teeth and jaws.

Figure 6:
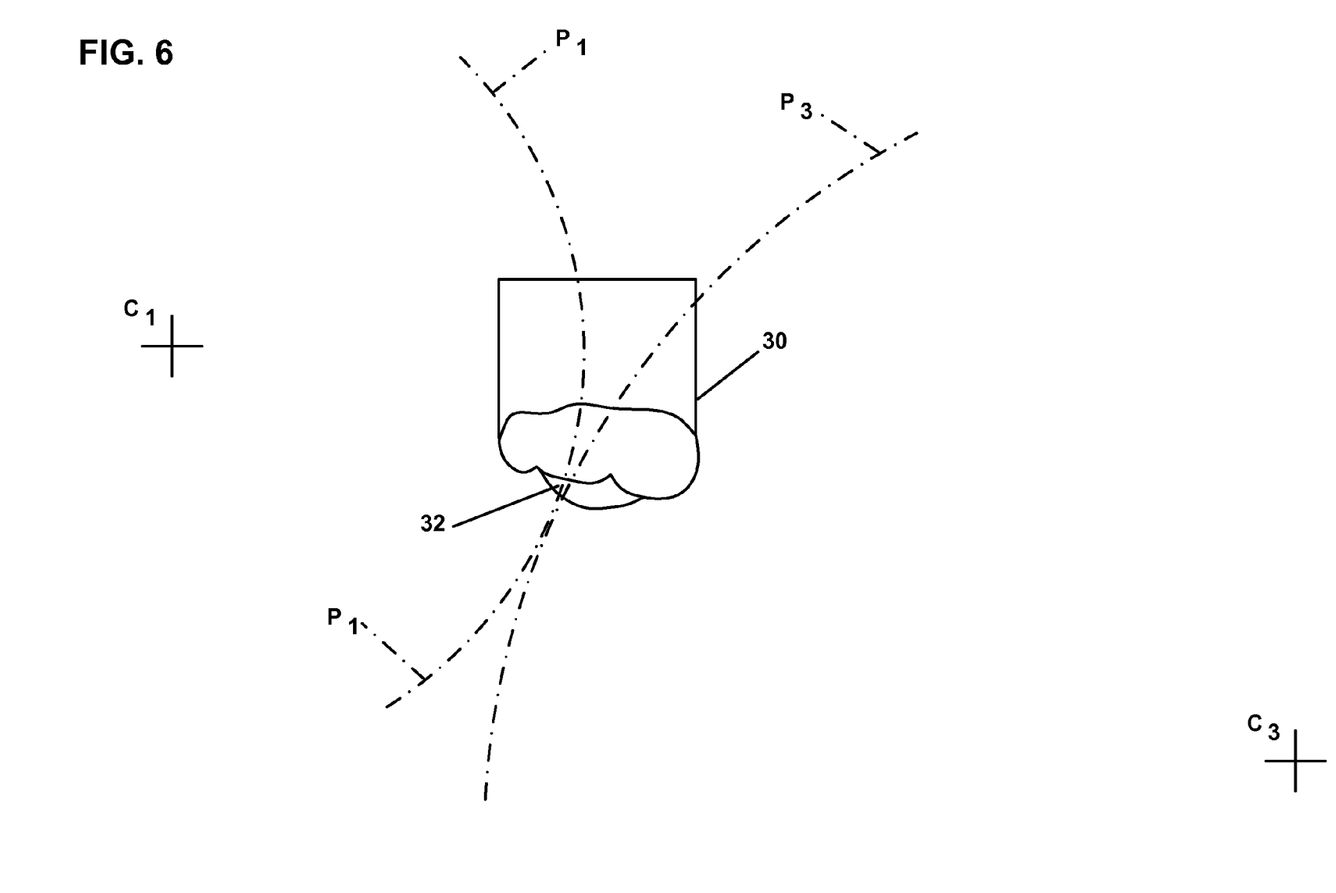
FIG. 6 is a perspective view of a projected path of movement for correction (with the instant center shifted-show 2)

Referring now to FIG. 6, there is shown a further example of a projected path and changes that may occur to move the instant center of rotation. For example, with some treatments, such as the application of corrective braces to the tooth, the instant center of rotation may move from a rotational axis shown at C1 in FIG. 4 to a rotational axis centered at C3, as shown in FIG. 6. The forces change the instant center of rotation and move the projected path of movement from path P1 to path P3. Although the rotational axis at the instant center C1 is moved from slightly above and behind the tooth 30 to a location in front of and below the tooth 30 to rotational axis point C3, the instant center of rotation may begin and end in any combination of places and it can be readily appreciated that the locations are shown only as examples. Other surrounding physiology and corrective devices may alter the center of rotation and/or the projected path. In a method of the present invention, the change is factored as a force vector acting on the tooth. For patients where tooth growth will occur, a growth coefficient may be factored to determine how much movement will occur over a predetermined period.

For some patients, the center of rotation may be positioned far from the tooth 30 and the length of the associated radius may approach infinity so that substantially linear motion is projected for the path of movement. The projected path of movement may be modeled with the digitized virtual model to occur on all three planes so that the projected center of rotation may also be positioned laterally from the patient's face. Such projected path of movement is easier to plot and represent in a digitized virtual model with greater precision, such as shown in FIG. 1, and provides, greater feedback and improved information for the dental practitioner to evaluate for proper treatment. Moreover, as the present invention provides for plotting paths of movement about various potential shifted centers of rotation, multiple different treatment approaches having different forces may be modeled. Therefore, different types of braces or other corrective measures may be evaluated by plotting the different centers of rotation and the corresponding projected path of movement. Modeling movement with precision leads to optimizing tooth position, diagnosis and correction.

Figure 8:
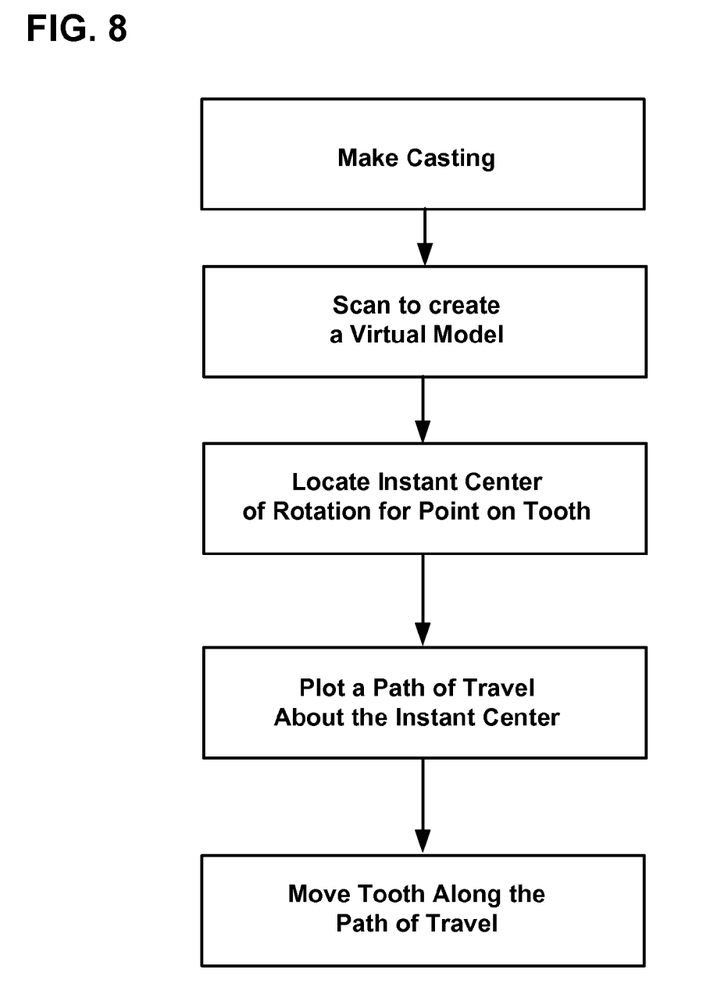
FIG. 8 is a flow chart showing the steps to model tooth movement according to the principles of the present invention.

Referring now to FIG. 8, to create a projection of tooth movement about an instant center of rotation, the model of the casting of the tooth is made and scanned into the memory 86 of the scanning system 80 as shown in FIG. 7. The patient's physiology and the virtual model are analyzed to locate an instant center of rotation for a particular tooth. Based upon the instant center of rotation, a projected path of movement is plotted. Using a time and force factor, a direction and distance along the projected path of movement is selected. The tooth is then repositioned with the projection point located along the path of movement the selected distance in the selected direction. A digital image is then created showing the tooth at the new location. It can be appreciated that such an image can be superimposed over the old location and combined with individual digital images of the other teeth and facial structures to create a complete new three dimensional image of the patient's teeth to simulate movement. Many virtual images can be superimposed to compare and optimize treatments.

Figure 9:
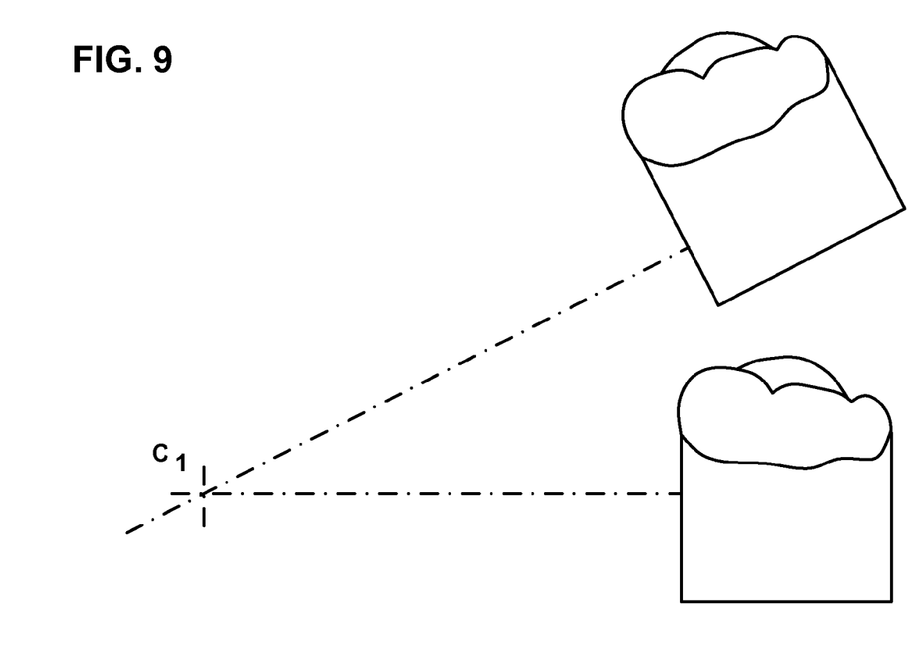
FIG. 9 is a diagrammatic view of the virtual model shown in FIG. 3 at two points in time to determine an instant center of rotation.

Referring now to FIG. 9, the present invention also provides for tracking of tooth movement through time by comparing and mapping the position of a tooth 30 over time. Such changes in position allow for further projection by locating a center of rotation by triangulating the center point from the tooth orientation at each of the positions. Such triangulation provides a center of rotation that can be used to plot a path of movement P4 about a center of rotation C4 and having a radial cord R4. The historical movement also provides for modifying the selected center of rotation and for reevaluating treatment.

Figure 10:
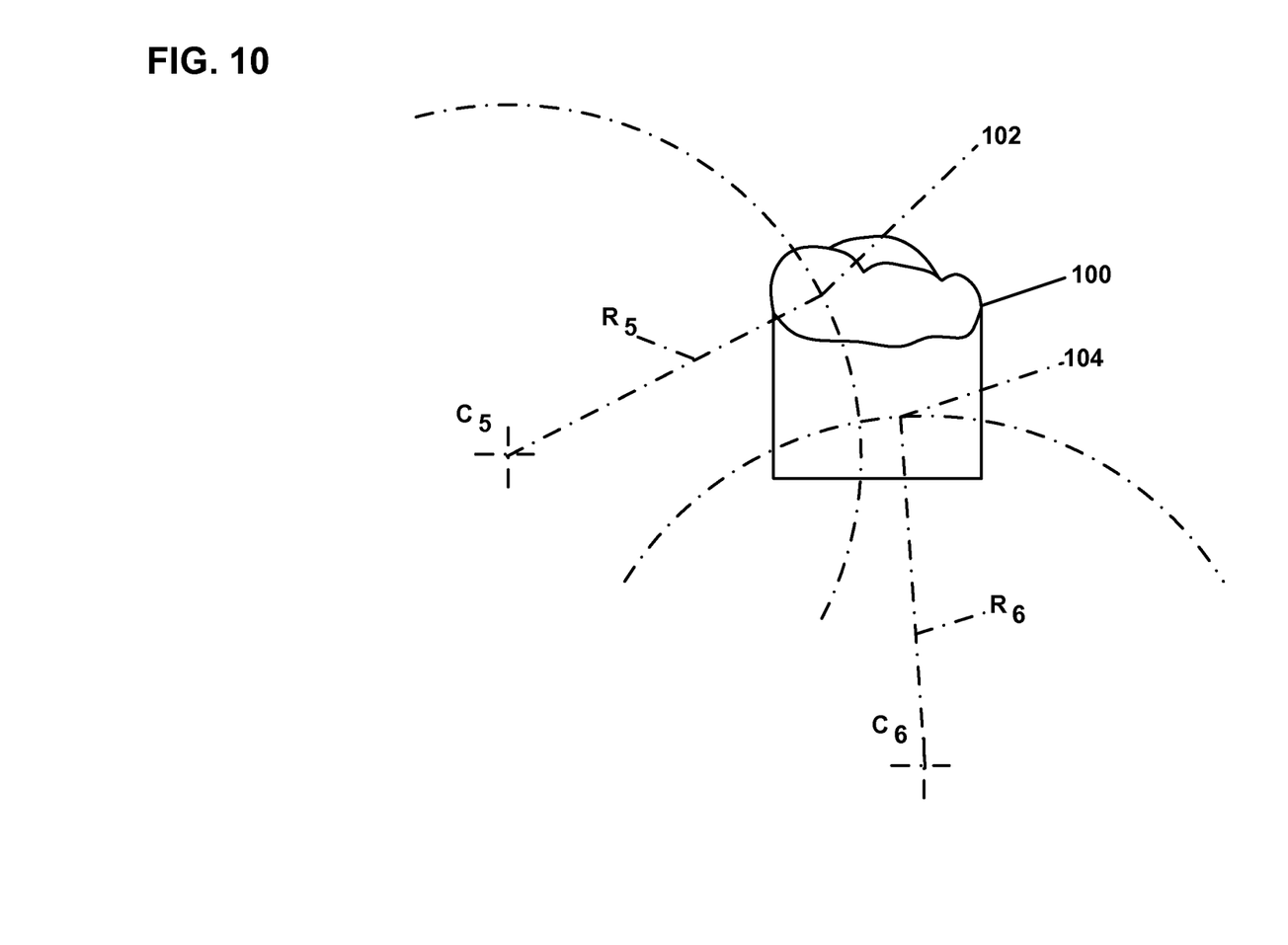
FIG. 10 is a diagrammatic view of a tooth with two points plotting a path of movement about an instant center of rotation for each point.

Referring now to FIG. 10, the present invention also provides for modeling growth for movement that does not follow rotation about a single center of rotation for a particular structure, such as a tooth 100. The tooth 100 and its movement may be represented as having a first point 102 following a path of movement centered about a first rotational axis C5, while a second point 104 of the tooth structure 100 may follow movement centered about a second instant center of rotation C6. Each of the locations 102 and 104 has a corresponding path of rotation, P5 and P6 respectively, and radial cords R5 and R6. In this manner, it can be appreciated that the movement of the tooth 100 over time may still be plotted with the tooth 100 having the same motion as a four bar linkage. It can be appreciated that the centers of rotation C5 and C6 act as the ground or first link while the radial chords R5 and R6 represent two other links. A tooth structure itself 100 represents a virtual fourth link. It can be appreciated that the rotational center points C5 and C6 may shift as explained above. The paths of movement P5 and P6 would also shift and movement of the two points 102 and 104 would follow a different four bar linkage, with the tooth reorienting and/or moving. Modeling techniques and treatment discussed above for a single instant center may also be employed for a tooth having movement behaving as a virtual four bar linkage.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A method of projecting tooth travel of a patient, comprising:
    creating a first virtual model of the patient's teeth;
    identifying a first reference point on a first virtual tooth of the model;
    identifying a second reference point on the patient's mandible;
    creating a second virtual model of the patient's teeth after a time period;
    tracking the travel of the first reference point from a first location to a second location over the time period;
    tracking the travel of the second reference point from a third location to a fourth location over the time period;
    extending a first segment between the first location and the second location;
    extending a second segment between the third location and the fourth location;
    projecting a first perpendicular bisector from the first segment;
    projecting a second perpendicular bisector from the second segment;
    determining an intersection of the first and second bisectors;
    defining a rotational axis;
    plotting an arc centered on the rotational axis along which the first reference point will travel.

2. A method according to claim 1, wherein a computer projects tooth travel in the future and creates a third virtual model representing a future tooth position.

3. A method according to claim 1, wherein the rotational axis is remote from the patient's teeth.

4. A method of projecting a patient's tooth travel on linkage configurations comprising:
    defining an instant axis of rotation of a tooth;
    adopting a first point on the patient's ramus as a first link pivot;
    adopting a second point on one of the patient's lower teeth as a second link pivot;
    tracing a first path of the first point pivoting about the instant axis of rotation, tracing a second path of rotation centered on the instant axis of rotation;
    advancing the first point along the first path a first distance;
    applying a relative movement factor to the first distance to determine a second distance;
    advancing the second point along the second path the second distance to arrive at a predicted location.

5. A method according to claim 4, wherein the instant axis of rotation of a tooth is remote from the tooth.

6. A method of projecting a patient's tooth travel on linkage configurations, comprising:
    defining a ground point axis of rotation;
    adopting a first point on the patient's ramus as a first link pivot;
    adopting a second point on one of the patient's lower teeth as a second link pivot;
    tracing a first path of the first point pivoting about the axis of rotation;

tracing a second path of rotation about the axis of rotation pivoting about the axis of rotation;

advancing the first point along the first path a first distance;

applying a relative travel factor to the first distance to determine a second distance between the first point and the second point;

advancing the second point along the second path until the second point is the second distance from the first point to arrive at a predicted location.

7. A method according to claim 6, wherein the linkage is oriented with virtual modeling.

8. A method according to claim 6, wherein the ground point axis of rotation is determined with virtual models.

9. A method according to claim 6, growth factor to determine distance between two pivots.

10. A method according to claim 6, wherein coefficient of relative growth is applied to the first distance to determine the second distance.

11. A method according to claim 6, wherein the ground point axis of rotation is remote from the one of the patient's lower teeth.

12. A method of projecting a patient's tooth travel on linkage configurations, comprising:

defining a ground point axis of rotation;

adopting a first point on the patient's ramus as a first link pivot and a segment connecting the axis of rotation and the first point as the first link;

adopting a second point on one of the patient's lower teeth as a second link pivot and a segment connecting the axis of rotation and the second point as the second link;

rotating the first point along the first path a first angle; applying a relative travel factor to the first angle to determine a second angle between the first segment and the second segment;

advancing the second link along the second path the second angle to arrive at a predicted location.

13. A method according to claim 12, wherein the first link is a driven link.

14. A method according to claim 13, wherein the first link is on the patient's ramus.

15. A method according to claim 12, wherein the ground point axis of rotation is remote from the one of the patient's lower teeth.

16. A method of projecting tooth travel, comprising:

creating a virtual model of a patient's mouth;

selecting an element as a link in a virtual four-bar linkage for projecting travel;

determining a first instant center of rotation associated with a first location on the element;

determining a second instant center of rotation associated with a second location on the element;

tracing a path of travel through the first location and centered on the first instant center of rotation;

tracing a path of travel through the second location and centered on the second instant center of rotation; and tracing a path of travel for the element with the first location centered on the first instant center of rotation and the second location centered on the second instant center of rotation, wherein the pivots in the four-bar linkage are at the first location, the second location, the first instant center of rotation and the second instant center of rotation.

17. A method according to claim 16, wherein at least one of the first instant center of rotation and the second instant center of rotation is remote from the element.

* * * * *

UNITED STATES PATENT AND TRADEMARK OFFICE
CERTIFICATE OF CORRECTION

PATENT NO. : 8,725,465 B2
APPLICATION NO. : 12/540233
DATED : May 13, 2014
INVENTOR(S) : Hultgren et al.

Page 1 of 1

It is certified that error appears in the above-identified patent and that said Letters Patent is hereby corrected as shown below:

In The Claims

Col. 8, line 53, claim 4: "a relative movement factor" should read --a relative travel factor--

Signed and Sealed this
Twenty-third Day of June, 2015

Michelle K. Lee
*Director of the United States Patent and Trademark Office*